United States Patent [19]

Pennig

[11] Patent Number: 4,988,349

[45] Date of Patent: Jan. 29, 1991

[54] DEVICE FOR OSTEOSYNTHESIS

[75] Inventor: Dietmar Pennig, Münster, Fed. Rep. of Germany

[73] Assignee: Orthofix S.r.l., Blussolengo VR, Italy

[21] Appl. No.: 552,345

[22] Filed: Jul. 16, 1990

Related U.S. Application Data

[63] Continuation of Ser. No. 273,818, filed as PCT DE88/00017 on Jan. 14, 1988, published as WO88/05287 on Jul. 28, 1988, abandoned.

[30] Foreign Application Priority Data

Jan. 21, 1987 [DE] Fed. Rep. of Germany .... 3701533.8

[51] Int. Cl.$^5$ .............................................. A61B 17/60
[52] U.S. Cl. ....................................... 606/58; 606/57; 606/59
[58] Field of Search ............................. 606/54–59, 606/72

[56] References Cited

U.S. PATENT DOCUMENTS

| | | | |
|---|---|---|---|
| 4,127,119 | 11/1978 | Kronner | 606/59 X |
| 4,135,505 | 1/1979 | Day | 606/59 |
| 4,308,863 | 1/1982 | Fischer | 128/92 ZZ |
| 4,312,336 | 1/1982 | Danieletto et al. | 128/92 ZZ X |
| 4,475,546 | 10/1984 | Patton | 128/92 ZZ X |
| 4,548,199 | 10/1985 | Agee | 128/92 Z K |
| 4,554,915 | 11/1985 | Brumfield | 128/92 Z X |
| 4,714,076 | 12/1987 | Compte et al. | 128/92 ZW |
| 4,730,608 | 3/1988 | Schlein | 128/92 ZK X |
| 4,745,913 | 5/1988 | Castaman et al. | 128/92 Z X |

FOREIGN PATENT DOCUMENTS

| | | | |
|---|---|---|---|
| 140591 | 5/1985 | European Pat. Off. | 128/92 Z |
| 563968 | 7/1977 | U.S.S.R. | 128/92 Z |
| 421788 | 6/1934 | United Kingdom | 128/92 ZZ |
| 2038638 | 7/1980 | United Kingdom | 128/92 Z |

OTHER PUBLICATIONS

The Salford Technique, Banks et al., 4/1980.
External Fracture Fixation Kenwright et al. 7/1979.

*Primary Examiner*—Robert A. Hafer
*Assistant Examiner*—Kevin G. Rooney
*Attorney, Agent, or Firm*—Peter K. Kontler

[57] ABSTRACT

A device for promoting the healing of bones has a pair of elongated carriers which support screws to be anchored in bone structure. The screws are movable longitudinally of the carriers by means of spindles. The carriers are joined to one another by a connector consisting of a rigid rod having a ball at either end. The balls are received in part-spherical sockets formed in the respective carriers and can be fixed relative to the carriers via screws.

17 Claims, 1 Drawing Sheet

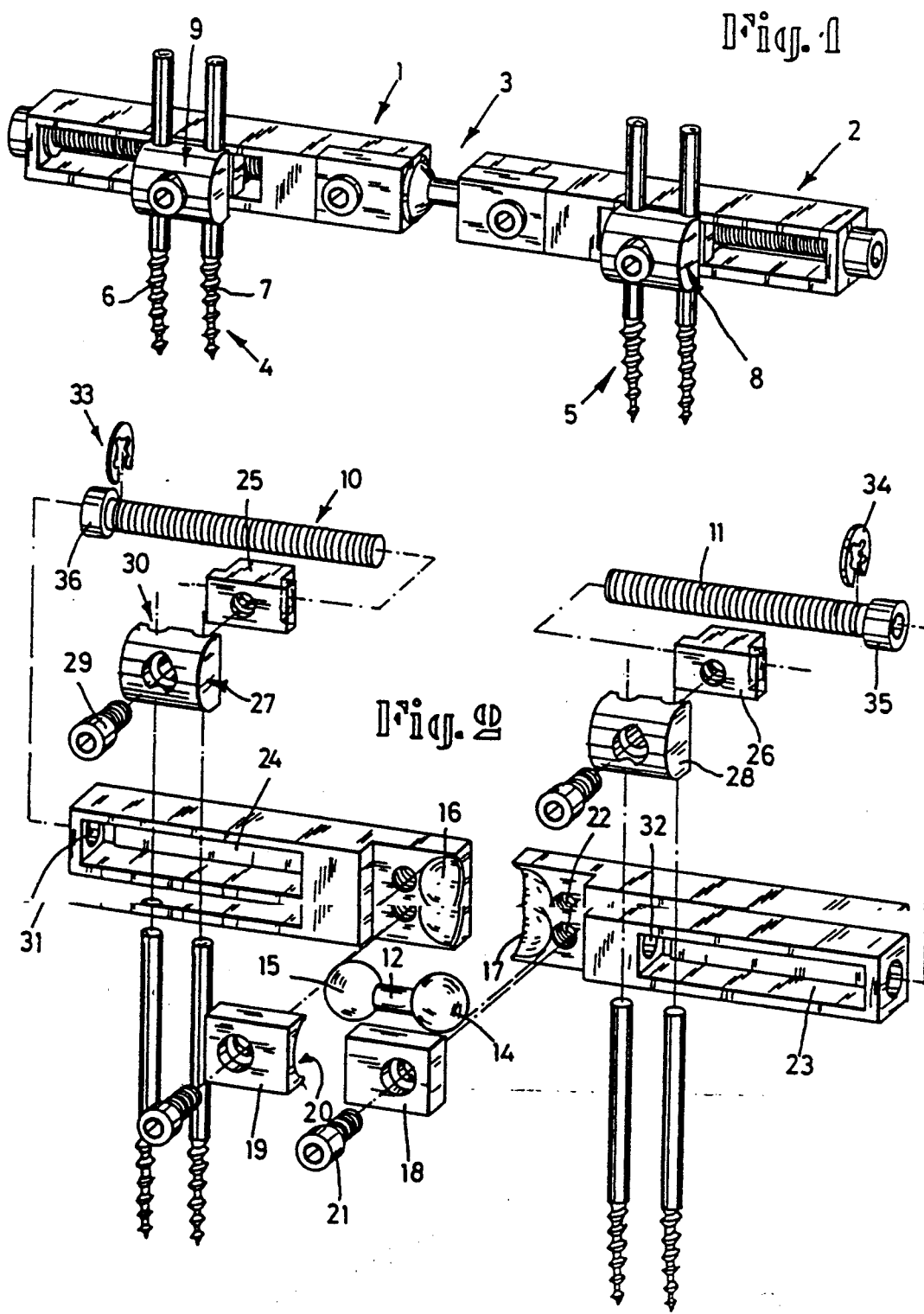

DEVICE FOR OSTEOSYNTHESIS

This application is a continuation of application Ser. No. 273,818, filed as PCT DE88/00017 on Jan. 14, 1988, published as WO88/05287 on Jul. 28, 1988, now abandoned.

The invention relates to a device for osteosynthesis.

Devices for osteosynthesis, particularly metallic devices, function to set a fracture. For bent, arched or curved bone segments, e.g., in jaw surgery, fixing of the fracture ends precisely in the desired and required position is very difficult, particularly when—as is currently conventional—the devices are to be completely covered, that is, applied internally.

An osteosynthesis device of this character is known from U.S. Pat. No. 1,789,060. With this device, setting of the fracture is effected outside of the body and such device consists essentially of two support plates which carry the setting members so that they are adjustable longitudinally of the support plate and so that their height relative to the support plate can be adjusted. Pivotal movement of the setting members on the support plates is not possible. The two support plates are joined to one another by a complicated hinge which consists, on the one hand, of two relatively adjustable hemispheres capable of being arrested relative to one another and, on the other hand, of an elongated guide slot in each support plate. The elongated slots of the two support plates are perpendicular to one another so that the height of one of the support plates and the transverse position of the other support plate can be regulated. This arrangement provides for alignment of the bone in a discontinuous manner only and, for fractures of complicated arched bones such as, for example, jawbones or dorsal vertebrae, only limited alignment of the fracture is possible due to the limited degrees of freedom of the osteosynthesis device.

It is an object of the invention to create an osteosynthesis device for the setting of fractures which makes it possible to achieve a large pivot angle of the two support plates relative to one another and allows alignment of the bone to be accomplished continuously so that the work of the surgeon is simplified.

An osteosynthesis device according to the invention makes it possible to achieve a large pivot angle of the two support plates relative to one another via a double-ball hinge and a spacer disposed between the two balls, and further makes it possible to adjust each individual support plate for itself in all directions.

The mounting of the setting members on the support plates for pivotal movement and height adjustment as additionally provided by the invention creates additional degrees of freedom for the overall arrangement which make it possible to carry out even the most complicated bone settings and alignments.

With the osteosynthesis device according to the invention, it is thus possible to first apply the setting members to the bone segments to be joined, to then connect the support plates, to then place the support plates at the desired angle, e.g., under an x-ray screen, and align the bone parts with respect to one another, and to then completely fix the entire osteosynthesis device as regards its adjustability. The design according to the invention takes account of the two setting errors which commonly occur, namely, rotation of the two separated bone parts and shifting of the two bone parts in two different planes.

An exemplary embodiment of the invention is described below with reference to the drawings in which:

FIG. 1 is a schematic overall view of the osteosynthesis device; and

FIG. 2 is an exploded view illustrating the individual components of the device shown in FIG. 1 in order to clarify the function of the individual elements.

In FIG. 1, 1 and 2 denote two support plates which are connected to one another by a double-ball hinge 3. The support plates carry setting members 4 and 5 with the setting members in the illustrated exemplary embodiment each consisting of two screws 6 and 7 which can be fixed to the support plates.

The setting members are fixed to the support plates by means of small fastening supports 8 and 9 and these small fastening supports are mounted on the support plates 1 and 2 for adjustment longitudinally thereof. Fixing of the small fastening supports 8 and 9 and their adjustment takes place via screw spindles 10 and 11, respectively.

The double-ball hinge 3 consists of two balls 14 and 15 which are connected to one another by a rigid spacer 12 and lie in ball sockets 16 and 17 having the shape of a quarter of a sphere and located at the ends of the support plates 1 and 2. Fixing of the balls occurs via ball socket plates 18 and 19 which are likewise formed with recesses in the shape of a quarter of a sphere. The recess 20 provided in the ball socket plate 19 and shaped like a quarter of a sphere is visible in FIG. 2. Attachment of the ball socket plates 18 and 19 is effected by means of screws 21 which screw into corresponding bores 22 in the support plates. By tightening the screws 21 to a greater or lesser degree, it is possible for the double-ball hinge 3 to be movable to all sides or to be rigid.

Slide guides 23 and 24 are provided in the support plates 1 and 2 and respectively guide sliding blocks 25 and 26 on which a respective clamping member 27 or 28 can be screwed, e.g., via the screws 29. Each clamping member 27 and 28 has two receiving spaces 30 conforming to the shape of the nails 6 and 7. By appropriately tightening the screws 29, the positions of the nails 6 and 7 can be fixed. Upon loosening the screws 29, rotation of the clamping members 27 and 28 out of the positions shown in FIG. 1 is possible so that the orientations of the screws 6 and 7 can be regulated.

The sliding blocks 25 and 26 are received in the slide guides 23 and 24 and have—as is observable in the drawing—a bore provided with internal threads which mesh with the external threads of the screw spindles 10 and 11. Each screw spindle 10 and 11 is fixed in the slide guide 23 or 24 by guiding the shaft of the screw spindle 10 or 11 in a respective opening 31 or 32 and placing an elastic snap ring 33 or 34 on the shaft. The enlarged head 35 or 36 of the screw spindle 10 constitutes the abutment for the elastic snap ring 33 or 34.

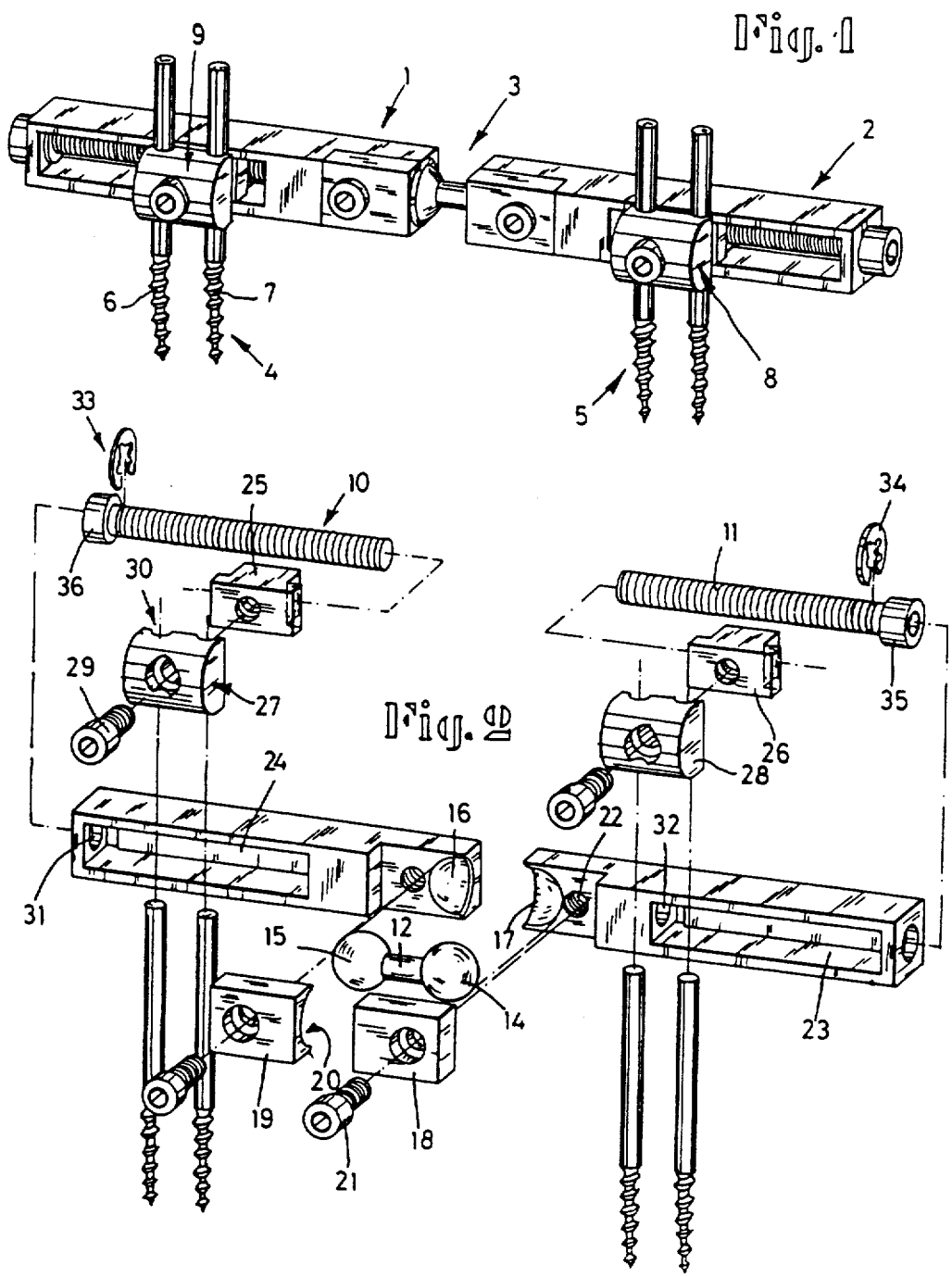

I claim:

1. A device for promoting the healing of bones, comprising first and second supports having confronting end portions; at least one anchoring member separably mounted on each of said supports and designed to be anchored in bone structure; a substantially barbell-shaped connector for joining the confronting end portions of said supports to one another, said connector including first and second at least approximately spherical elements each mountable on the end portion of the respective support, and a spacer rigidly connecting said elements to one another, said device being free of protrusions extending between said supports and the interiors of the respective elements, the end portion of each of said supports being provided with a first socket having the configuration of a quarter of a sphere; and means for arresting said connector relative to said supports, including first and second confining members distinct from and arranged to cooperate with the respective supports and including second part spherical sockets complementary to the respective first sockets, each of said elements being receivable in the respective first and the respective second socket to establish a universal joint between said spacer and the respective support.

2. The device of claim 1, wherein at least one of said supports is elongated and further comprising means for mounting said at least one anchoring member for said elongated support for movement longitudinally of said elongated support.

3. The device of claim 2, wherein said mounting means includes means for arresting said at least one anchoring member for said elongated support at any one of a plurality of positions longitudinally of said elongated support.

4. The device of claim 1, wherein at least one of said anchoring members comprises a screw or a nail.

5. The device of claim 1, wherein at least one of said supports is elongated and further comprising means for mounting said at least one anchoring member for said elongated support for movement longitudinally of said elongated support, said mounting means including a clamping member movable longitudinally of said elongated support and designed to clamp said at at least one anchoring member to said elongated support.

6. The device of claim 5, wherein said clamping member is designed to permit pivoting of said at least one anchoring member for said elongated support relative to said elongated support.

7. The device of claim 6, wherein said mounting means includes means for fixing said at least one anchoring member for said elongated support in any one of a plurality of angular positions relative to said elongated support.

8. The device of claim 1, wherein said at least one anchoring member for said elongated support is elongated and said clamping member is designed to permit shifting of said at least one anchoring member relative to said elongated support in longitudinal direction of said at least one anchoring member for said elongated support.

9. The device of claim 6, wherein said mounting means includes means for fixing said at least one anchoring member for said elongated support in any one of a plurality of positions relative to said elongated support as considered in longitudinal direction of said at least one anchoring member for said elongated support.

10. The device of claim 5, wherein said mounting means includes a guide passage extending longitudinally of said elongated support, and a holder movable along said passage and connectable to said clamping member.

11. The device of claim 10, wherein said holder has a first side arranged to face said clamping member and said clamping member has a second side arranged to face said holder, said first side being substantially flat and substantially complementary to said at least one anchoring member for said elongated support.

12. The device of claim 1, wherein a least one of said supports is elongated and further comprising means for moving said at least one anchoring member for said elongated support for movement longitudinally of said elongated support, said mounting means including a guide passage extending longitudinally of said elongated support, and a holder movable along said passage and designed to carry said at least one anchoring member for said elongated support.

13. The device of claim 12, wherein said mounting means includes a rotatable drive member having an externally threaded shaft designed to extend longitudinally of said passage, said holder being provided with an internally threaded bore arranged to mesh with said shaft.

14. The device of claim 13, further comprising means for fixing said drive member against movement longitudinally of said passage, said fixing means including a resilient member designed to snap onto said drive member.

15. The device of claim 14, wherein said resilient member is ring-like.

16. The device of claim 1, wherein said spacer has a fixed length.

17. The device of claim 2, wherein said elongated support has a longitudinal axis and said mounting means is designed to permit pivoting of said at least one anchoring member for said elongated support relative to said elongated support on an axis which is transverse to said longitudinal axis.

* * * * *

UNITED STATES PATENT AND TRADEMARK OFFICE
CERTIFICATE OF CORRECTION

PATENT NO. : 4,988,349           Page 1 of 2
DATED      : January 29, 1991
INVENTOR(S): Dieter Pennig It is certified that error appears in the above-indentified patent and that said Letters Patent is hereby corrected as shown below:

Fig. 2 should be deleted and substitute therefor Fig. 2, as shown on the attached page.

Col. 1, line 63, after "two" insert --possible--.

Signed and Sealed this

Twenty-first Day of September, 1993

Attest:

BRUCE LEHMAN

Attesting Officer    Commissioner of Patents and Trademarks

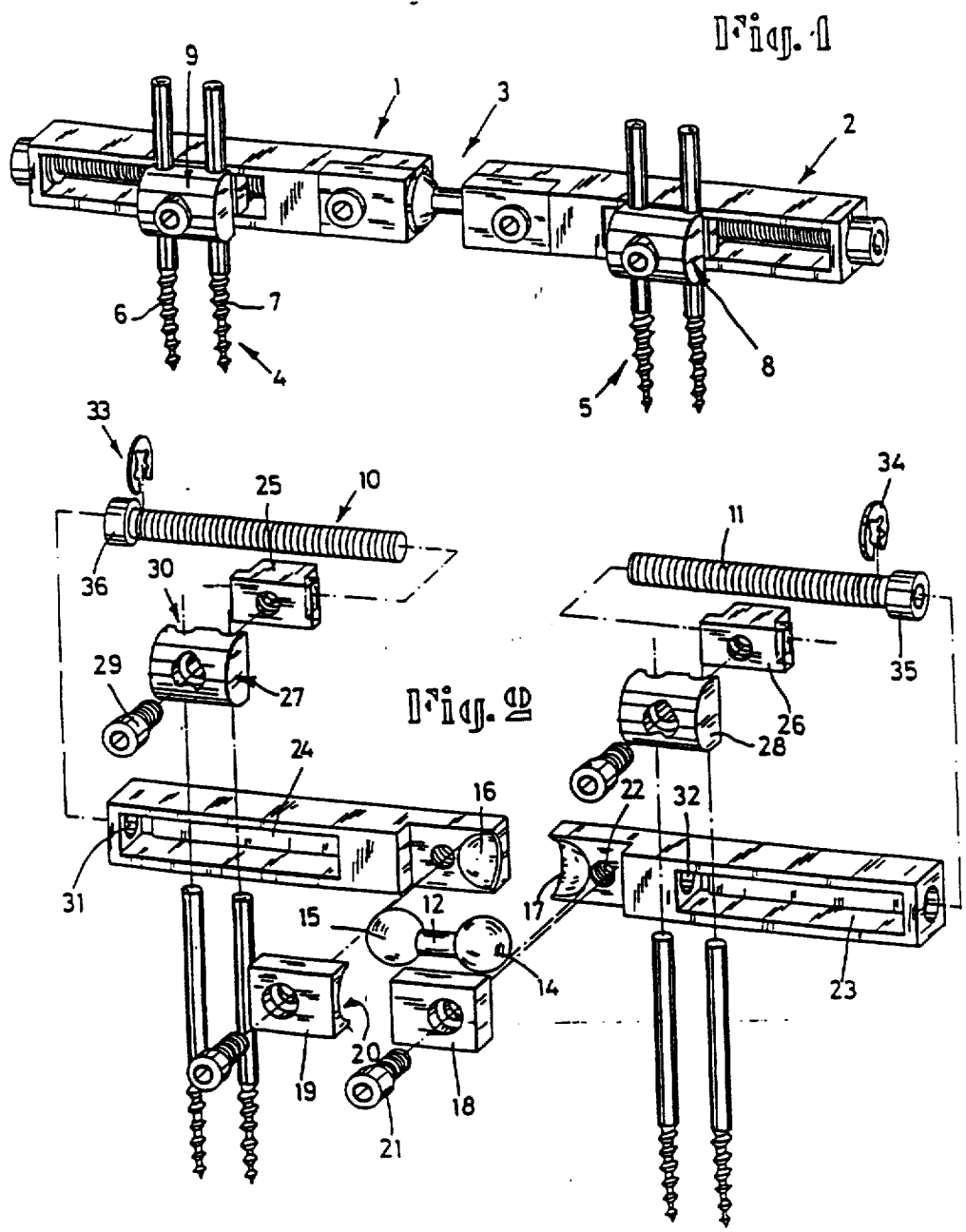

UNITED STATES PATENT AND TRADEMARK OFFICE
CERTIFICATE OF CORRECTION

PATENT NO.  : 4,988,349  
DATED       : January 29, 1991  
INVENTOR(S) : Dieter Pennig Page 1 of 2

It is certified that error appears in the above-indentified patent and that said Letters Patent is hereby corrected as shown below:

The drawing sheet, consisting of Fig. 2, should be deleted to be replaced with the drawing sheet, consisting of Fig. 2, as shown on the attached page.

Column 1, line 63, after "two" insert --possible--

Column 2, line 1, delete "overall" and insert --perspective--

This Certificate supersedes Certificate of Correction issued September 21, 1993.

Signed and Sealed this

Sixteenth Day of November, 1993

*Attest:*

BRUCE LEHMAN

*Attesting Officer*     *Commissioner of Patents and Trademarks*